United States Patent
Glavind et al.

(10) Patent No.: US 9,255,886 B2
(45) Date of Patent: Feb. 9, 2016

(54) SYSTEM AND METHOD FOR DETECTING DAMAGE TO A WIND TURBINE BLADE

(75) Inventors: Lars Glavind, Randers C (DK); Ib Svend Olesen, Randers (DK); Mark Hancock, Southampton (GB); Richard Craven, Cowes (GB)

(73) Assignee: Vestas Wind Systems A/S, Aarhus N. (DK)

( * ) Notice: Subject to any disclaimer, the term of this patent is extended or adjusted under 35 U.S.C. 154(b) by 0 days.

(21) Appl. No.: 13/984,190

(22) PCT Filed: Feb. 14, 2012

(86) PCT No.: PCT/DK2012/050053
§ 371 (c)(1),
(2), (4) Date: Jan. 21, 2014

(87) PCT Pub. No.: WO2012/110041
PCT Pub. Date: Aug. 23, 2012

(65) Prior Publication Data
US 2014/0151578 A1   Jun. 5, 2014

Related U.S. Application Data (60) Provisional application No. 61/442,932, filed on Feb. 15, 2011.

(30) Foreign Application Priority Data

Feb. 15, 2011  (GB) .................................. 1102640.8

(51) Int. Cl.
*F21V 9/16* (2006.01)
*G01J 1/42* (2006.01)
(Continued)

(52) U.S. Cl.
CPC ........ *G01N 21/8806* (2013.01); *F03D 11/0091* (2013.01); *G01M 5/0016* (2013.01);
(Continued)

(58) Field of Classification Search
CPC .......... G01N 21/6428; G01N 21/6458; G01N 21/6408; G01N 21/645; G01N 21/6452; G01N 2021/6421; G01N 21/64; G01N 21/6456; G01N 21/6402
USPC .......... 250/459.1, 458.1, 461.1, 462.1, 461.2, 250/462.2
See application file for complete search history.

(56) References Cited

U.S. PATENT DOCUMENTS 4,492,121 A   1/1985  Lehto
5,387,791 A   2/1995  Weiss
(Continued)

FOREIGN PATENT DOCUMENTS

EP   2112374 A1   10/2009
GB   2467295 A    7/2010
(Continued)

OTHER PUBLICATIONS

Grattan et al., "Luminescent optical fibers in sensing", 1998, Kluwer Academic Publishers, London ISBN 0 412 84420 6. Optical Fiber Sensor Technology, vol. 4. Edited by K. T. V. Grattan and B. T. Meggitt. pp. 1-43.*

(Continued)

*Primary Examiner* — David Porta
*Assistant Examiner* — Mamadou Faye
(74) *Attorney, Agent, or Firm* — Patterson & Sheridan, LLP (57) ABSTRACT

A system and method of detecting damage to a wind turbine blade uses one or more fluorescent optical fibers comprising a fluorescent material having an excitation wavelength that is selected such that the material fluoresces upon exposure to ambient radiation at the wind turbine blade, wherein the one or more optical fibers are operatively mounted within the wind turbine blade such that upon damage to the wind turbine blade at least a part of the optical fiber is exposed at the surface of the blade causing the optical fiber to fluoresce; a light detector for receiving a light signal from one or from both ends of the one or more optical fibers upon excitation of the fluorescent material and outputting a signal based on the light signal; and a controller coupled to the light detector to receive the signal.

30 Claims, 2 Drawing Sheets (51) Int. Cl.
*G01N 21/88* (2006.01)
*G01M 11/08* (2006.01)
*G01M 11/02* (2006.01)
*F03D 11/00* (2006.01)
*G01M 5/00* (2006.01)
*G01N 21/64* (2006.01)

(52) U.S. Cl.
CPC .......... *G01M5/0033* (2013.01); *G01M 5/0091* (2013.01); *G01M 11/0278* (2013.01); *G01M 11/083* (2013.01); *G01M 11/085* (2013.01); *G01N 21/64* (2013.01); *G01N 21/6447* (2013.01); *Y02E 10/722* (2013.01)

(56) References Cited

U.S. PATENT DOCUMENTS

| | | | |
|---|---|---|---|
| 6,710,328 B1 * | 3/2004 | Mastro et al. | 250/227.14 |
| 7,356,228 B1 | 4/2008 | Berens et al. | |
| 2009/0257242 A1 * | 10/2009 | Wendman | 362/553 |
| 2009/0262331 A1 * | 10/2009 | Burchardt et al. | 356/32 |
| 2012/0119074 A1 * | 5/2012 | Johnston | 250/227.14 |

FOREIGN PATENT DOCUMENTS

| | | |
|---|---|---|
| GB | 2469427 A | 10/2010 |
| WO | 2001035084 A1 | 5/2001 |

OTHER PUBLICATIONS

International Search Report and Written Opinion; PCT/DK2012/050053; Jul. 5, 2012.

Combined Search and Examination Report (UK Patent Office); GB 1102640.8; Mar. 25, 2011.

* cited by examiner

SYSTEM AND METHOD FOR DETECTING DAMAGE TO A WIND TURBINE BLADE

The present invention relates to an optical fibre system and method for the detection of damage to a wind turbine blade during use. The invention finds particular application in the detection of delamination of a composite material forming a wind turbine blade component, as well as in the detection of surface erosion or corrosion of a wind turbine blade.

The wind turbine blades of commercial wind turbines are typically formed of composite materials, which are capable of withstanding the stress and loading to which the blade will be subjected during operation of the turbine. In rare cases, defects can occur within the composite materials forming a wind turbine blade and this may have an adverse effect on the mechanical integrity of the blade. Defects may arise as a result of discontinuities in the material that have been introduced during manufacture of the blade, for example, during lay-up of the fibres forming the composite material. Alternatively, in some cases defects may arise as a result of excessive strain or loading on the blade during operation of the turbine.

Some of the most common types of defects occurring in the composite materials forming wind turbine blades include the delamination or separation of the layers forming the composite material and/or cracking of the material. Due to the high loading of the wind turbine blades during operation, such delamination or cracking can spread rapidly through the composite material, resulting in structural damage to the blade and in severe cases, failure of the wind turbine.

It is known to incorporate systems to monitor wind turbine blades during operation in order to detect damage to the composite material of the blade. For example, EP-A-2 112 374 discloses a crack detection system for a wind turbine blade which comprises a network of optical fibres embedded within the blade. The presence of a crack running substantially perpendicularly to the blade surface is detected by detecting sudden changes in the transmission of light through the optical fibres, which occur as a result of breakage of the fibre as the crack propagates.

Damage to a wind turbine blade can also occur as a result of erosion of the blade surface during operation, in particular at the leading edge of the blade. This may be caused by exposure to harsh environmental conditions such as rain, hail or sand. Chemical erosion, or corrosion, is also a problem for offshore wind turbines. The gradual wearing away of the blade surface due to erosion can adversely affect the aerodynamic properties of the blade, for example, as a result of turbulence at the eroded surface. The overall efficiency of the extraction of energy from the wind is therefore reduced.

It would be desirable to provide an improved system and method for monitoring wind turbine blades during operation, which enables defects or damage to the composite material forming the blade to be detected at an early stage so that the blade can be repaired before the damage worsens. It would also be desirable if such a system and method could be adapted to detect a variety of types of damage or defects in the composite material. In particular, it would be desirable to provide a system and method which can be adapted for detecting delamination or erosion of the composite material forming the blade.

According to a first aspect of the invention there is provided a system of detecting damage to a wind turbine blade comprising: one or more fluorescent optical fibres comprising a fluorescent material that is selected such that the material fluoresces upon exposure to ambient radiation at the wind turbine blade; a light detector for receiving a light signal from one or from both ends of the one or more optical fibres upon excitation of the fluorescent material and outputting a signal based on the light signal; and a controller coupled to the light detector to receive the signal. The one or more fluorescent optical fibres are operatively mounted within the wind turbine blade such that upon damage to the wind turbine blade at least a part of the optical fibre is exposed at the surface of the blade causing the optical fibre to fluoresce.

According to a second aspect of the invention there is provided a method of detecting damage to a wind turbine blade, the method comprising the steps of: providing one or more optical fibres within the composite material forming the wind turbine blade, wherein the one or more optical fibres comprise a fluorescent material that is selected such that the material fluoresces upon exposure to ambient radiation at the wind turbine blade; connecting at least one end of the one or more optical fibres to a light detector mounted on the wind turbine comprising the wind turbine blade; operating the light detector to detect light emitted from the fluorescent material upon exposure of the one or more optical fibres at the surface of the blade as a result of damage to the blade and to output a signal when light is detected; and receiving the signal at a controller.

According to a third aspect of the invention there is provided a use of one or more fluorescent optical fibres to detect damage to a wind turbine blade, wherein the one or more fluorescent optical fibres comprise a fluorescent material that is selected such that the material fluoresces upon exposure to ambient radiation at the wind turbine blade.

The term 'fluorescent material' is used to refer to a material that has the property of absorbing radiation of one or more specific wavelengths and subsequently re-emitting the energy from the absorbed radiation as light of different, usually longer, wavelengths. In the context of the present invention, the term 'fluorescent material' encompasses any type of material that emits light upon excitation by a form of ambient radiation, including for example fluorescent materials that are excited by electromagnetic waves such as visible and UV light, and scintillation materials that are excited by ionising radiation such as gamma rays, photons or charged particles.

The term 'ambient radiation' is used to refer to any type of radiation that is naturally present in the atmosphere or environment surrounding the wind turbine blade. The system and method of the present invention relies upon excitation of the fluorescent material by radiation present in the atmosphere and does not need to incorporate a separate radiation source within the wind turbine in order to function effectively. The required apparatus for monitoring the wind turbine blade to detect damage is therefore simpler and more cost effective to produce and run than other types of optical fibre systems requiring a light source for directing light into the optical fibres.

The ambient radiation at the wind turbine blade under normal conditions typically includes but is not limited to visible light, infrared radiation, ultraviolet radiation, gamma rays, photons or other types of naturally occurring ionising particles. In the system and method of the present invention, the fluorescent material in the optical fibres may be selected to fluoresce upon excitation by any type of radiation that will be present in the atmosphere at the wind turbine and which will be incident upon the optical fibre upon damage to the wind turbine blade. Fluorescent materials are often particularly sensitive to light in the UV region of the electromagnetic spectrum and the fluorescent optical fibres used in the system and method of the present invention therefore preferably fluoresce upon excitation by UV light. Other suitable fluorescent materials may be excited by electromagnetic radiation in the form of visible light or infrared radiation.

The system and method of the present invention provide an effective way of monitoring a wind turbine blade during operation in order to rapidly detect defects or damage to the blade and provide an early warning that damage has occurred. This enables the damaged part of the blade to be repaired or replaced at an early stage before the condition of the blade deteriorates to a stage where the damage results in failure of the wind turbine or irreversible structural damage. The system and method of the present invention also enable the wind turbine blades to be properly maintained so that any damage to the blade does not adversely affect the aerodynamic properties of the blade.

Damage to a wind turbine blade may result from internal defects in the composite material forming the blade that have been inadvertently introduced into the material during manufacture, such as air or resin pockets within the layered structure. Such defects introduce a point of weakness within the composite material that can trigger the formation of a crack in the material, or delamination of the fibrous layers when the blade is subjected to heavy loading during operation. Damage may alternatively occur to the wind turbine blade as a result of external conditions such as excessive forces or loading on the wind turbine blade, or erosion or corrosion of the blade surface due to adverse atmospheric or weather conditions. The system and method of the present invention may be readily adapted to detect any of these types of damage, as described in more detail below.

The system and method of the present invention rely on one or more fluorescent optical fibres that are positioned within the wind turbine blade so that upon a particular type of damage to the blade at least a part of the one or more optical fibres is uncovered and exposed at the surface of the blade. This exposure may be brought about, for example, by cracking or splitting of the composite material to expose a part of an embedded optical fibre, or by the removal or regression of the composite material overlying the optical fibre. Ambient radiation is then incident upon the exposed part of the optical fibre and causes the fluorescent material incorporated in the optical fibre to fluoresce and emit a light signal, which is reflected down the fibre to the light detector. The detection of fluorescence from the material is therefore indicative of damage to the blade.

The system of the present invention produces an output signal as soon as at least a part of the fluorescent optical fibre is exposed to ambient radiation. This will typically be before the damage propagates to an extent that the optical fibre is broken or eroded. In this way, the system and method of the present invention can advantageously detect damage to the blade at a relatively early stage and in many cases without damage or destruction of the optical fibres.

The system and method of the present invention can advantageously be adapted to monitor different parts of the wind turbine blade for different types of damage, in particular, through the specific placement of the one or more fluorescent optical fibres within the blade. As described in more detail below, the one or more fluorescent optical fibres are positioned within the blade such that a particular type of damage to the blade will cause the optical fibre to become exposed to the ambient radiation at the blade.

Under normal working conditions, the one or more fluorescent optical fibres are enclosed within the composite material forming the wind turbine blade and are therefore not exposed to significant levels of ambient radiation. Under normal conditions, the fluorescent material will therefore typically not fluoresce and little or no light will be detected by the light detector. As discussed above, the system of the present invention does not require any internal excitation source (although in some cases an internal light source may be incorporated, as described below) and the light detector will only be required to emit an output signal in the event of damage to the blade, resulting in fluorescence of the optical fibre. This means that the system of the present invention can be used to provide a 'passive' system that requires minimal or no power input to monitor the blade under normal conditions. The cost of operating the system is therefore also minimal and in addition, the system has a very long lifetime and can monitor continuously for long periods without replacement of components.

The light detector of the system of the present invention is connected to one or both ends of each fluorescent optical fibre in order to receive light that has been generated by the fluorescent material upon exposure of the optical fibre to ambient radiation. The light detector may take any suitable form, including but not limited to known devices such as photomultipliers, photodetectors, photodiodes or PIN diodes, for detecting the light associated with the fluorescence of the optical fibre. The light detector receives the light from the fluorescent optical fibres and converts it to a signal, such as an electrical signal, which it transmitted to the controller to generate a warning signal that damage has occurred.

The light detector may be operatively mounted within the wind turbine blade but preferably, the light detector is operatively mounted on a stationary part of the wind turbine on which the wind turbine blade is mounted. For example, in preferred embodiments, the light detector is mounted within the hub of the wind turbine and the one or more fluorescent optical fibres are connected to the light detector either directly, or indirectly by means of one or more non-fluorescent optical fibres.

The controller may be integrated with the light detector, or may be a separate component which is connected to the detector with suitable wires or cables, or using a wireless connection. Where the controller is a separate component, it may be provided within the turbine or at a remote location. Suitable devices for use as the controller would be known to the skilled person.

Preferably, the system of the present invention comprises means for measuring the levels of ambient radiation at the wind turbine and transmitting this information to the controller. The light signal from the one or more fluorescent optical fibres can then be processed taking into account the level of ambient radiation that is incident on the blade. This enables the system to adapt to different conditions, for example, different light conditions during different parts of the day.

In certain preferred embodiments, the system of the present invention comprises a network of a plurality of fluorescent optical fibres operatively located within a specific area or region of the wind turbine blade for detecting damage within that area or region. This type of network arrangement increases the coverage of the detection system so that damage can be detected within a larger area or region. In addition, the use of a network of fluorescent optical fibres enables the position of the damage to be readily identified based on the light signals received from the network of optical fibres, and for any propagation of the damage to be monitored.

In one particular preferred example of a system according to the invention, a plurality of substantially parallel fluorescent optical fibres is provided. An arrangement of parallel optical fibres is particularly suitable for the detection of cracks in the composite material and the monitoring of the propagation of the crack, or for the monitoring of corrosion or erosion at the surface of the blade. The term 'parallel' is intended to indicate that the optical fibres extend through the blade so that the general orientations of the fluorescent optical fibres are parallel. However, adjacent optical fibres may not be exactly parallel to each other at every point along their length, for example, where the optical fibres are not provided in linear configurations.

The one or more fluorescent optical fibres of systems according to the invention are operatively embedded or integrated within the composite material forming the wind turbine blade so that the optical fibres are not exposed to ambient radiation under normal conditions. Typically, such the optical fibres will be integrated or embedded within the composite material during manufacture of the wind turbine blade, for example, during the moulding process. The embedding of optical fibre sensors within a composite wind turbine component is a well known process which is used for the incorporation of optical fibre sensors intended for monitoring the component during operation of the turbine, such as strain sensors.

The one or more fluorescent optical fibres may be embedded within the interior of the composite material, for example, between the layers of fibrous material forming the blade. With this arrangement, the system and method of the present invention can be employed to detect cracks in the composite material forming the blade. In some cases, the cracks may propagate through the material in a direction that is substantially perpendicular to the length of the blade, or at an angle to the layers of the material. In other cases, cracks may propagate through the material along the length of the blade, for example between the layers. The system and method of the present invention is suitable for the detection of cracks in both cases.

In a first preferred embodiment, the system is adapted for detecting delamination within a composite material by operatively embedding the one or more fluorescent optical fibres between layers of the composite material. Preferably, the one or more fluorescent optical fibres are embedded under the surface of the composite material forming the blade so that even relatively small cracks or splits at the surface will be detected. Upon delamination, during which certain layers of the composite material break apart or split, one or more of the fluorescent optical fibres are exposed to ambient radiation, causing excitation of the fluorescent material and the emission of light. Upon receiving the emitted light from the fluorescent material, the light detector emits a signal to the controller to indicate that delamination has occurred.

Delamination has been found to occur most often at the leading edge or trailing edge of the blade and the fluorescent optical fibres of systems for detecting delamination of the composite material forming the blade can therefore most effectively be incorporated along these edges.

The system and method of the present invention provide for the first time an effective way of detecting delamination of the composite material forming the blade, in which a crack or split forms and propagates along the length of the blade, in the direction of the layers. Where the fluorescent optical fibres are provided underneath the surface of the blade, even cracks of a relatively short length can be detected so that the damage can be detected at a very early stage before the crack propagates further along the blade. In the systems of the prior art, the optical fibres are arranged in order to detect cracks propagating in a direction that is substantially parallel to the blade surface and the layers of the composite material. Generally, only cracks propagating in this direction will cause the breakage of the optical fibres in order to generate a warning signal of damage. This type of prior art arrangement is therefore not suitable for reliably detecting delamination of the composite material forming a blade.

Systems for detecting delamination, cracking, or other types of damage that are likely to occur as a result of excessive loading on the wind turbine blades may advantageously be positioned in areas of the blade components where the loading or forces exerted on the blade are likely to be highest, such as for example in the central spar or at the leading edge.

In a second preferred embodiment, the system is adapted for detecting erosion or corrosion of a surface of the wind turbine blade by embedding the one or more fluorescent optical fibres a small distance underneath the external surface of the blade. Upon erosion of the composite material overlying the one or more fluorescent optical fibres proximate the external surface, the one or more fluorescent optical fibres are exposed to ambient radiation, causing excitation of the fluorescent material and the emission of light. Upon receiving the emitted light from the fluorescent material, the light detector emits a signal to the controller to indicate that a certain level of erosion has been reached.

The system and method of the present invention provide an effective way to detect erosion of the surface of the blade at a relatively early stage so that steps can be taken to repair the erosion damage before it worsens. Erosion can otherwise be difficult to monitor, since the reduction in power output from the turbine as a result of the surface erosion may be difficult to detect until the erosion has reached a significant level. As described above, prior art systems for detecting blade damage typically rely on the breakage of one or more optical fibres. Again, it will therefore not be possible to detect erosion of the blade surface until the erosion has reached a significant level.

Systems according to the second embodiment of the invention for detecting erosion or corrosion may be particularly beneficial for use in offshore turbines, which are often positioned in remote locations and in harsh environments. Maintenance of offshore turbines is typically relatively high cost and the system of the present invention advantageously provides an early warning of erosion of the blade, which can reduce the cost and time associated with the necessary repair or maintenance.

The fluorescent optical fibres of systems according to the present invention can advantageously be provided in regions of the wind turbine blade that are most susceptible to damage from erosion. For example, the one or more fluorescent optical fibres may be provided along the leading edge of the blade where erosion may be more significant. Where the one or more fluorescent optical fibres are provided at the leading edge, preferably a plurality of optical fibres is provided covering approximately 5 to 10% of the chord of the wind turbine blade at the leading edge. Alternatively or in addition, the one or more fluorescent optical fibres may be positioned towards the tip end of the blade, furthest from the hub, where erosion is likely to be more significant due to the higher speed of the blade tip. Where the one or more fluorescent optical fibres are provided at towards the tip end, the optical fibres preferably extend approximately 20 to 30% of the length of the blade at the tip end.

Systems according to the present invention for detecting erosion may be further improved by incorporating a material with optical properties between the one or more fluorescent optical fibres and the surface of the blade. For example, the one or more fluorescent optical fibres may be covered by the optical material. The optical material is selected such that upon erosion of the blade surface to reveal the underlying optical material, light or other ambient radiation will be transmitted by the material from the blade surface where damage has occurred to the one or more fluorescent optical fibres, thereby causing the fluorescent material within the optical fibres to fluoresce and emit light to the light detector. This means that the fluorescent optical fibres can be caused to fluoresce upon damage to the blade surface even before the damage has reached the optical fibres, as a result of the transmission of the ambient radiation by the optical material.

Such an optical material may also advantageously be provided in systems for detecting other types of damage to a wind turbine blade, in order to detect damage at an even earlier stage. For example, such an arrangement may be beneficial for detecting damage that occurs during transport of the blade, which will typically be caused by a small number of hard strokes on the blade. Materials, such as lacquers or varnishes, having suitable optical properties would be known to the skilled person.

According to the present invention there is provided a wind turbine blade incorporating a system according to the invention for detecting damage to the blade, as described above. Systems according to the invention are preferably incorporated into each blade of a wind turbine and a plurality of separate systems according to the invention may be used in a single blade to detect different types or locations of damage, if desired.

According to the invention there is further provided a wind turbine comprising at least one wind turbine blade incorporating the system of the present invention for detecting damage to the blade, as described above.

The one or more fluorescent optical fibres of the systems of the present invention will typically comprise a core and an outer cladding. The fluorescent material may be provided mainly in the core, mainly in the cladding, or in both the core and the cladding. Where the fluorescent material is provided in the core alone, the cladding must be such that the ambient radiation for exciting the fluorescent material can pass through the cladding to the core. The fluorescent material may be incorporated in the optical fibre by doping or by dissolving the material into the fibre material during production. Alternatively, the fluorescent material may be provided in a coating layer on the optical fibre.

When the fluorescent optical fibres are exposed to ambient radiation at the surface of the wind turbine blade, at least some of the radiation is absorbed by the fluorescent material in the fibre. The absorbed energy is then re-emitted isotropically inside the fibre, typically as light of a longer wavelength. Some of the re-emitted light is subject to total internal reflection in the interior of the fibre and therefore travels along the length of the fibre until it is received at the light detector.

The core of the fluorescent optical fibre may be made of glass, quartz, or plastic. Plastic Optical Fibres (POF) include those made from PMMA (polymethyl methacrylate), polystyrene, polycarbonate (PC), or other suitable polymers, including fluorinated plastics such as perfluorinated polymers. The cladding may be of a similar material to the core, with a suitable refractive index for total internal reflection to occur over the likely wavelength of remitted light, or more generally include one or more plastic materials, either alone or in a blend, such as PMMA, PVDF (Polyvinylidene Fluoride) or fluorinated polymers. Any suitable width of optical fibre can be used. For example, the width of the optical fibre can be in the range 0.125 mm to 5 mm.

Suitable materials for the fluorescent material may be one or more naturally occurring or synthetic fluorescents, such as perylene dye, or BBOT (5-tert-butyl-2-benzoxazolyl thiophene), samarium ions ($Sm^{3+}$), or any suitable rare earth metals. Fluorescent and scintillator fibre optic cables available commercially can also be used.

It is generally important that the fluorescent material is insensitive to the wavelengths of light that it re-emits, so that self-absorption in the fibre does not occur and the light can propagate along the fibre unobstructed, and that the wavelength of the light that is emitted is such that total internal reflection within the fibre will occur. The combination of the fibre materials and the fluorescent material must therefore be selected accordingly.

In some cases it may be advantageous to use a blend of two or more fluorescent materials for the doping in order to ensure optimal capture of the ambient radiation upon exposure of the optical fibre. In certain embodiments, the fluorescent optical fibre can be doped with two or more fluorescent materials so that double fluorescence occurs. The first fluorescent material can be selected so that its absorption spectrum is sensitive to the likely spectrum of ambient radiation. The second (or further fluorescent materials) can be selected to be sensitive to both the ambient radiation, and the radiation emitted by the first fluorescent material. Where two different fluorescent materials are provided in the optical fibre, the fluorescent materials may be provided in the same or a different location to each other. For example, the first material may be provided in the core of the optical fibres whilst the second material is provided within the cladding.

Preferably, both ends of a fluorescent optical fibre are connected to the light detector to that, even if there were to be a break in the fibre, detection of the light collected in the fibre upon damage to the blade will still be possible from at least one end of the fibre.

In some cases, the system and method of the present invention may be more effective at detecting damage to the blade during the daytime when levels of certain types of ambient radiation, such as visible light, are higher. At night time, the levels of human generated radiation, such as from artificial lighting, may be sufficient for the system to operate effectively upon damage to the blade. The light generated by external lights already mounted on the wind turbine, such as aircraft warning lights, may also be sufficient for the excitation of the fluorescent material so that the system can work effectively during darkness.

If desired, one or more external radiation sources may be provided on the wind turbine or adjacent the wind turbine such that radiation emitted from the source is incident on the area of the blade being monitored for potential damage. The radiation source may be a light source, which operates to emit light in low light conditions, for example during night time. Alternatively, the radiation source may emit ultraviolet or infrared radiation. The use of an external source with infrared radiation may be advantageous in some locations, in order to reduce light pollution and any interference of the radiation source with aircraft warning lights. The wavelength of radiation emitted from the external source should be selected to correspond to the excitation wavelength of the fluorescent material in the one or more fluorescent optical fibres of the system of the present invention.

Alternatively or in addition to providing an external radiation source, the system of the present invention may further comprise an internal radiation source provided within the blade proximate the fluorescent optical fibres, wherein the internal radiation source emits radiation at a wavelength corresponding to the excitation wavelength of the fluorescent material.

Preferably, the internal radiation source comprises one or more light emitting optical fibres connected to a light source, wherein the light directed down the fibres is emitted out through the cladding of the fibres. The cladding is therefore preferably substantially transparent. Preferably, the light source is mounted within the hub of the wind turbine and the light emitting optical fibres are embedded within the blade and extend through the portion of the blade alongside the fluorescent optical fibres, separated by a small thickness of composite material.

Under normal conditions, the fluorescent optical fibres will be separated from the light emitting optical fibres by the composite material between them and therefore the fluorescent material in the fluorescent fibres is not exposed to the light from the light emitting optical fibres. Upon damage to the blade, such as delamination or cracking in the region between the fluorescent optical fibres and the light emitting optical fibres, the fluorescent material is then exposed to light from the light emitting fibres.

This arrangement incorporating an internal radiation source such as one or more light emitting optical fibres advantageously provides a back up system that ensures that the system and method of the present invention operate effectively, even in low light level conditions. In addition, the incorporation of an internal light source may advantageously enable the system and method of the present invention to detect internal damage to the wind turbine blade that may not otherwise be detected or which may only be detected at a later stage when the damage causes the fluorescent optical fibres to be exposed to ambient radiation.

Methods according to the invention of detecting damage to a wind turbine blade can be carried out using the apparatus described above. The one or more fluorescent optical fibres within the blade are connected to the light detector and the light detector is operated to detect light emitted from the fluorescent material upon exposure of the optical fibre to ambient radiation. The detection of light from one or more optical fibres indicates that damage has occurred to the blade which has broken or removed the composite material in such a way that at least a part of the optical fibre has been uncovered and exposed at the internal surface of the blade. This will be the first indication that damage to the blade has occurred.

In methods according to the invention, the controller preferably processes the output signal from the light detector in order to determine the location of the exposed fluorescent optical fibre. This may be facilitated through the use of a network of fluorescent optical fibres, as described above.

In certain preferred embodiments of the invention, the light detector may additionally be operated to detect degradation in the light received from one or more of the fluorescent optical fibres. Such a degradation or cessation of the light emitted from the fluorescent material is indicative of erosion or breakage of the fluorescent optical fibres such that the light can no longer be transmitted along the fibre. This may indicate a higher level of damage to the blade than when the initial light signal is received from the fluorescent material. Where a network or fluorescent optical fibres is provided, the pattern of degradation of the light received from the optical fibres may be used to track the location and/or propagation of the damage through an area of the blade.

Methods according to the invention may comprise embedding the one or more optical fibres between the layers of a composite material forming the wind turbine blade, as described above. Alternatively or in addition, methods according to the invention may comprise embedding the one or more optical fibres proximate the external surface of the wind turbine blade, as described above. The optical fibres may be embedded in positions of the blade where damage is most likely to occur, such as the leading edge, trailing edge or the tip end of the blade.

The present invention provides methods for detecting delamination of a composite material forming the wind turbine blade, as described above. The present invention further provides methods for detecting erosion or corrosion of the external surface of the blade, as also described above.

The invention will now be further described, by way of example only, and with reference to the accompanying figures in which.

Figure 1:
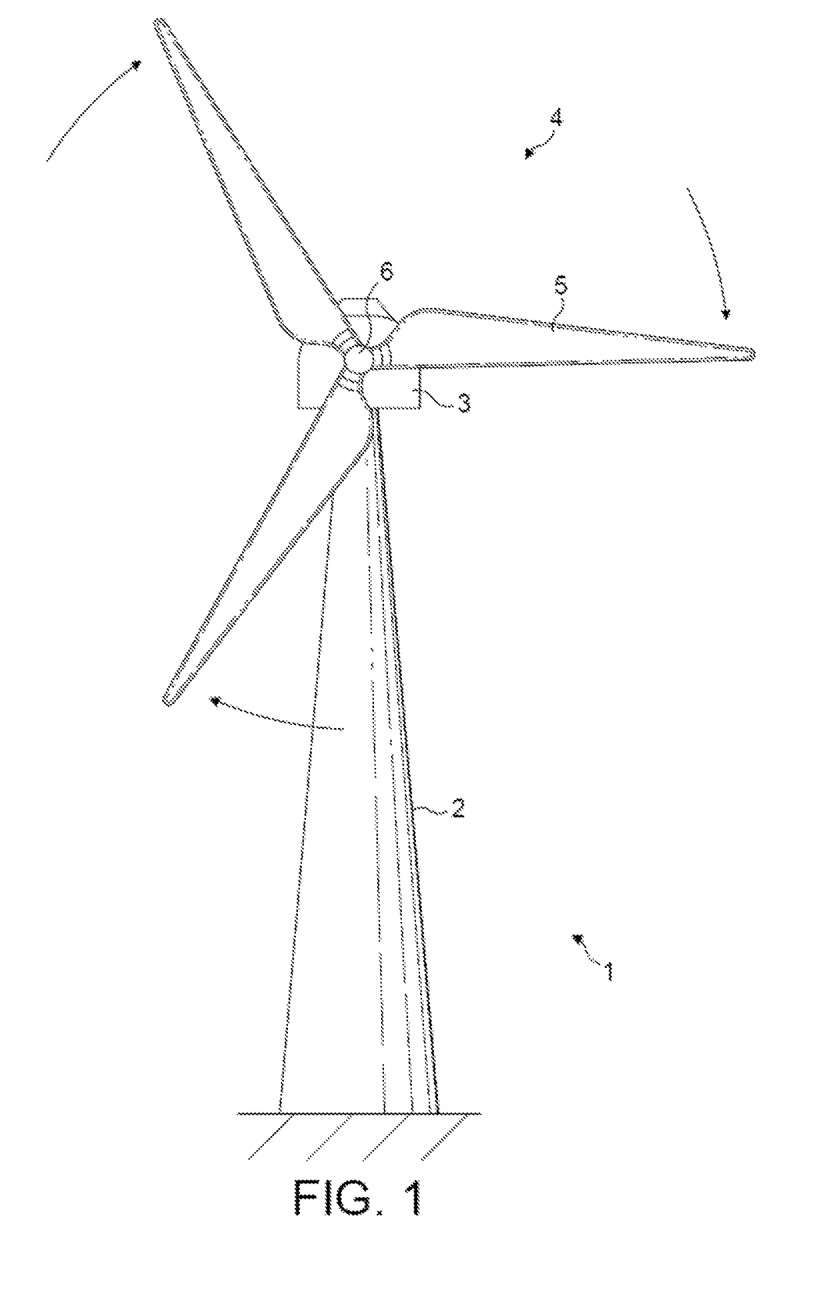
FIG. 1 is a front view of a horizontal axis wind turbine.

FIG. 1 illustrates a wind turbine 1, comprising a wind turbine tower 2 on which a wind turbine nacelle 3 is mounted. A wind turbine rotor 4 comprising three turbine blades 5 attached to a central hub 6 is mounted on the turbine. The wind turbine illustrated in FIG. 1 may be a small model intended for domestic or light utility usage, or for example may be a large model, such as those that are suitable for use in large scale electricity generation on a wind farm. In the latter case, the diameter of the rotor may be as large as 100 meters or more.

Each blade 5 incorporates a sensor arrangement 10 comprising a plurality of fluorescent optical fibres 12 each end of which is connected to a light detector 14, such as a photodiode, which is mounted within the hub 6. A controller (not shown) is connected to the light detector by connections, such as wires or cables.

Figure 2:
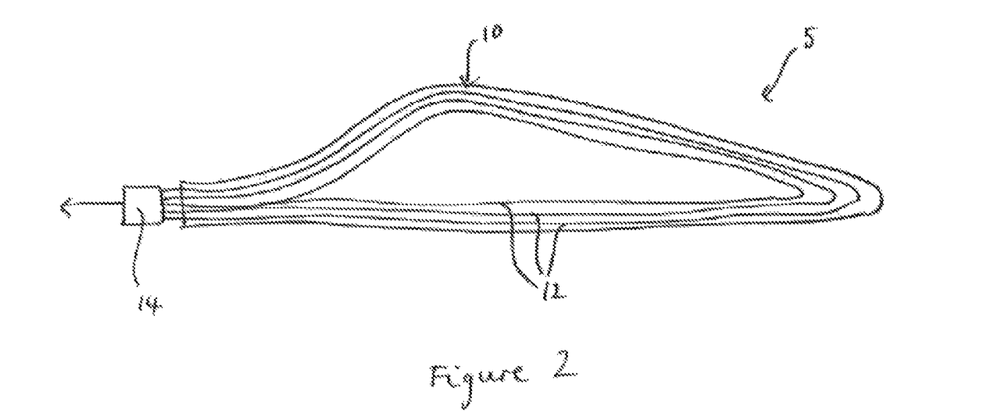
FIG. 2 is a schematic view of a wind turbine blade incorporating a system according to the first preferred embodiment for detecting delamination within the blade.

The sensor arrangement 10 is provided for detecting delamination in the composite material forming the outer shell of the wind turbine blades. As shown in FIG. 2, the plurality of fluorescent optical fibres 12 of the sensor arrangement run along the length of the wind turbine blade 5 and the fibres are spaced apart from each other through the shell, to form a network of substantially parallel optical fibres. Each fluorescent optical fibre 12 is embedded within the composite material forming the outer shell of the blade 5, between the fibrous layers of the composite material. Three parallel optical fibres are shown schematically in FIG. 2 but a higher or lower number may be provided.

Under normal operating conditions, the fluorescent optical fibres 12 will be enclosed within the composite material forming the blade shell and the intensity of light received at the light detector will be low or negligible. The sensor arrangement 10 operates by detecting any light emitted from the fluorescent material in one of the optical fibres, which has been reflected along the fibre to the light detector 14. Upon receiving the light from the fluorescent material, the light detector 14 generates an electrical output signal which is sent to the controller. The controller processes the output signal and can alert the operator to the occurrence of the damage.

In the event of delamination of the composite material of the outer shell, two or more of the fibrous layers of the composite material come apart from each other and typically a crack propagates through the material, in the direction of the length of the blade. When the crack reaches the external surface of the wind turbine blade 5, any parts of the fluorescent optical fibres 12 in the region of the crack will be exposed to ambient radiation. The fluorescent material in the exposed part of the optical fibres 12 will absorb the ambient radiation and will re-emit the energy as light, as described above.

If the crack propagates further, the fluorescent optical fibre 12 transmitting the light to the light detector 14 may be broken or snapped, so that the light cannot be transmitted through to both ends of the fibre. The light detector will detect a reduced intensity of light from the fibre and send an electrical output signal to the controller, which can be processed to indicate the location of the breakage of the optical fibre.

Figure 3:
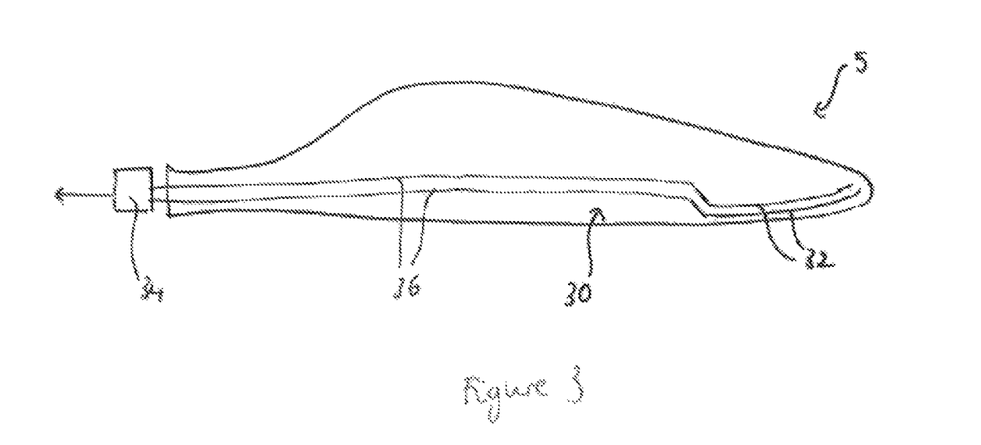
FIG. 3 is a schematic view of a wind turbine blade incorporating a system according to the second preferred embodiment for detecting erosion of the blade during transport.

FIG. 3 illustrates a blade with an alternative sensor arrangement 30 for detecting erosion at the external surface. The sensor arrangement 30 may be used in combination with the sensor arrangement 10, although it can alternatively be used separately.

The sensor arrangement 30 comprises a plurality of fluorescent optical fibres 32 embedded within the blade shell, a small distance underneath the surface. Each of the optical fibres 32 extends along approximately one quarter of the length of the blade 5 from the tip end and the fibres are spaced apart from each other around the leading edge of the blade at the tip end. Two parallel optical fibres are shown schematically in FIG. 3 but a higher or lower number may be provided.

As in the sensor arrangement 10 shown in FIG. 2, the arrangement 30 of FIG. 3 additionally comprises a light detector 34 which may be mounted in the hub of the turbine. The light detector is connected to an end of each fluorescent fibre 32 by means of non-fluorescent optical fibres 36, in order to receive any light transmitted along the fibres. A controller (not shown) is connected to both the light emitting device and light measuring device, by connections, such as wires or cables.

In the event of erosion of the external surface of the blade 5, the outer layers of the composite material forming the outer shell of the blade will be worn away and eventually, one or more of the fluorescent optical fibres 32 embedded below the surface will be exposed at the surface of the blade. The fluorescent material in the exposed part of the optical fibre will absorb the ambient radiation and will emit light which will be reflected down the optical fibre to the light detector 34.

As with sensor arrangement 10 described above, under normal operating conditions, the fluorescent optical fibres 32 will be enclosed within the composite material forming the blade shell and the intensity of the light received at the light detector will be low or negligible. The sensor arrangement 30 operates by detecting any light emitted from the fluorescent material in the optical fibre which has been reflected along the fibre to the light detector 34. Upon receiving the light from the fluorescent material, the light detector 34 generates an electrical output signal which is sent to the controller. The controller processes the output signal and can alert the operator to the occurrence of the erosion.

If the erosion continues, the fluorescent optical fibres 32 will themselves begin to erode and the light signal received from the optical fibre 32 may diminish. As with the sensor arrangement 10, when an optical fibre 32 is eroded entirely, the fibre may no longer be able to transmit the light to the light detector through the ends of the fibre and the detector will detect the change in the intensity of the light signal received.

The invention claimed is:

1. A system of detecting damage to a wind turbine blade, comprising:
   one or more fluorescent optical fibres operatively mounted within the wind turbine blade and comprising a fluorescent material having an excitation wavelength such that, upon damage to the wind turbine blade, at least a part of one or more fluorescent optical fibres is exposed to ambient radiation at a surface of the wind turbine blade causing the one or more fluorescent optical fibres to fluoresce;
   a light detector for detecting a light signal from at least one end of the one or more fluorescent optical fibres only upon excitation of the fluorescent material when the one or more fluorescent optical fibres is exposed to the ambient radiation and outputting a signal indicating damage to the wind turbine blade based on detection of the light signal; and
   a controller coupled to the light detector to receive the signal.

2. The system according to claim 1, wherein the fluorescent material comprises a scintillation material.

3. The system according to claim 1, wherein the light detector is operatively mounted on a stationary part of the wind turbine, wherein the wind turbine comprises the wind turbine blade.

4. The system according to claim 1, comprising a plurality of substantially parallel fluorescent optical fibres.

5. The system according to claim 1, wherein the wind turbine blade comprises a composite material, wherein the damage comprises at least delamination of the composite material, and wherein the one or more fluorescent optical fibres are operatively embedded between layers of the composite material such that, upon delamination, the one or more fluorescent optical fibres are exposed to the ambient radiation, causing the one or more fluorescent optical fibres to fluoresce.

6. The system according to claim 1, wherein the wind turbine blade comprises a composite material, wherein the damage comprises at least erosion of a surface of the wind turbine blade, and wherein the one or more fluorescent optical fibres are operatively embedded in the composite material proximate an external surface of the blade such that, upon erosion of the overlying composite material, the one or more fluorescent optical fibres are exposed to the ambient radiation, causing the one or more fluorescent optical fibres to fluoresce.

7. The system according to claim 1, further comprising a layer of an optical material operatively provided between the one or more fluorescent fibres and a surface of the wind turbine blade, wherein, upon exposure of the optical material to ambient radiation, the optical material transmits the ambient radiation to the underlying one or more fluorescent optical fibre, causing the one or more fluorescent optical fibres to fluoresce.

8. The system according to claim 1, wherein the one or more fluorescent optical fibres are operatively embedded at a leading edge or a trailing edge of the wind turbine blade.

9. The system according to claim 1, wherein the one or more fluorescent optical fibres are operatively embedded towards a tip end of the wind turbine blade.

10. The system according to claim 1, wherein the fluorescent material is excited by one or more of visible light, infrared and ultraviolet radiation.

11. The system according to claim 1, wherein the fluorescent material has an excitation wavelength configured to enable the fluorescent material to fluoresce upon exposure to ionising radiation.

12. The system according to claim 1, wherein the one or more fluorescent optical fibres each comprises a fibre core and an outer cladding, and wherein the fluorescent material is located mainly in the cladding.

13. The system according to claim 1, wherein the one or more fluorescent optical fibres each comprises a fibre core and an outer cladding, and wherein the fluorescent material is located mainly in the fibre core.

14. The system according to claim 1, wherein the one or more fluorescent optical fibres comprises one or more optical fibres having a fluorescent coating.

15. The system according to claim 1, wherein the one or more fluorescent optical fibres are connected to the light detector by one or more non-fluorescent optical fibres.

16. The system according to claim 1, further comprising an external radiation source mounted on or adjacent to the wind turbine blade such that radiation from the external radiation source is incident on the wind turbine blade, wherein a wavelength of the radiation corresponds to the excitation wavelength of the fluorescent material.

17. The system according to claim 1, further comprising an internal radiation source embedded within the wind turbine blade adjacent the one or more fluorescent optical fibres, wherein a wavelength of radiation from the internal radiation source corresponds to the excitation wavelength of the fluorescent material.

18. The system according to claim 17, wherein the internal radiation source comprises a light source and one or more light emitting optical fibres connected to the light source.

19. A method of detecting damage to a wind turbine blade, the method comprising the steps of:
   providing one or more fluorescent optical fibres within a composite material forming the wind turbine blade, wherein the one or more optical fibres comprise a fluorescent material having an excitation wavelength such that the fluorescent material fluoresces upon exposure to ambient radiation at the wind turbine blade;
   connecting at least one end of the one or more optical fibres to a light detector mounted on a wind turbine comprising the wind turbine blade;
   operating the light detector to detect light emitted from the fluorescent material only upon exposure of the one or more fluorescent optical fibres at the surface of the wind turbine blade as a result of damage to the wind turbine blade and to output a signal when light is detected to indicate the damage to the wind turbine blade; and
   receiving the signal at a controller.

20. The method according to claim 19, further comprising the step of operating the light detector to detect degradation in the light emitted from the one or more of the fluorescent optical fibres indicative of erosion or breakage of the one or more fluorescent optical fibres.

21. The method according to claim 19, further comprising the step of processing the signal at the controller to determine a location of the exposed one or more fluorescent optical fibres.

22. The method according to claim 19, comprising embedding the one or more fluorescent optical fibres between layers of the composite material.

23. The method according to claim 19, comprising embedding the one or more fluorescent optical fibres proximate the surface of the wind turbine blade.

24. The method according to claim 22, comprising embedding the one or more optical fibres at a leading edge of the wind turbine blade.

25. The method according to claim 19, wherein the damage comprises delamination of the composite material.

26. The method according to claim 19, wherein the damage comprises erosion or corrosion of the surface of the wind turbine blade.

27. The method according to claim 19, further comprising providing an optical material between the one or more fluorescent optical fibres and the surface of the wind turbine blade, wherein upon exposure of the optical material to the ambient radiation, the optical material transmits the ambient radiation to the underlying one or more fluorescent optical fibres, causing the one or more fluorescent optical fibres to fluoresce.

28. A wind turbine blade comprising the system of claim 1.

29. A wind turbine comprising one or more wind turbine blades incorporating the system of claim 1.

30. Use of one or more fluorescent optical fibres to detect damage to a wind turbine blade, wherein the one or more fluorescent optical fibres comprise a fluorescent material having an excitation wavelength such that the material fluoresces upon exposure to ambient radiation at the wind turbine blade only when damage to the wind turbine blade causes the one or more fluorescent optical fibres are exposed at a surface of the wind turbine blade.

* * * * *